United States Patent
Ma et al.

(10) Patent No.: US 11,421,234 B2
(45) Date of Patent: Aug. 23, 2022

(54) APTAMERS FOR TARGETING COAGULATION FACTOR XIII AND USES THEREOF

(71) Applicant: Chang Gung University, Taoyuan (TW)

(72) Inventors: Yunn-Hwa Ma, Taoyuan (TW); Ching-Ping Tseng, Taoyuan (TW); Kai-Wen Cheng, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 456 days.

(21) Appl. No.: 16/699,742

(22) Filed: Dec. 2, 2019

(65) Prior Publication Data
US 2021/0163945 A1    Jun. 3, 2021

(51) Int. Cl.
*C12N 15/115* (2010.01)
*A61K 48/00* (2006.01)
*A61K 47/54* (2017.01)
*A61K 45/06* (2006.01)

(52) U.S. Cl.
CPC ............ *C12N 15/115* (2013.01); *A61K 45/06* (2013.01); *A61K 47/549* (2017.08); *A61K 48/0058* (2013.01); *C12N 2310/16* (2013.01); *C12N 2310/351* (2013.01); *C12N 2310/3513* (2013.01); *C12N 2310/3517* (2013.01)

(58) Field of Classification Search
CPC .............. C12N 15/115; C12N 2310/16; C12N 2310/351; C12N 2310/3513; C12N 2310/3517
See application file for complete search history.

(56) References Cited

U.S. PATENT DOCUMENTS

2011/0097715 A1* 4/2011 Siret .................... C12N 9/6437
530/413

* cited by examiner

*Primary Examiner* — Ekaterina Poliakova-Georgantas

(57) ABSTRACT

Provided herein is an aptamer specific to coagulation factor XIII (FXIII) and its uses thereof. Accordingly, the present aptamer is useful as a bio-tool to label thrombi, and/or as a targeting molecule to deliver drugs to thrombotic area. Therefore, the present disclosure also pertains to methods for treating diseases associated with FXIII, such as thrombosis.

17 Claims, 3 Drawing Sheets
(2 of 3 Drawing Sheet(s) Filed in Color)
Specification includes a Sequence Listing.

FAT2                      N-DNA

APTAMERS FOR TARGETING COAGULATION FACTOR XIII AND USES THEREOF

BACKGROUND OF THE INVENTION

1. Field of the Invention

The present disclosure in general relates to an oligonucleotide aptamer. More particularly, the present disclosure relates to an oligonucleotide aptamer for targeting coagulation factor XIII (FXIII).

2. Description of Related Art

Aptamers are oligonucleotide (such as DNA, RNA or XNA), or peptide molecules that bind to a specific target molecule through their secondary or tertiary conformation fitting to the target. Generally, aptamers may be generated by the method "systematic evolution of ligands by exponential enrichment (SELEX)" which mainly comprises the process of in vitro screening a large random sequence library (usually comprising $10^{13}$ to $10^{16}$ nucleic acid molecules) against the target of interest, and selecting those that can specifically bind to the target. In terms of the purpose of targeting, oligonucleotide aptamers are advantageous over antibodies in many aspects. First, oligonucleotide aptamers can be chemically synthesized, thus the cost for producing oligonucleotide aptamers is cheap, and the quality in every batch may be kept the same. Moreover, contamination by bacteria, viruses, or prions may be prevented due to chemical synthesis. In addition, since the nature of oligonucleotide aptamers is nucleic acid, the shelf life of oligonucleotide aptamers is longer than that of antibodies. Besides that, oligonucleotide aptamers can be stored at room temperature, and are stable over pH and temperature variations. When given to human bodies, oligonucleotide aptamers rarely induced adverse immune responses. Those properties make oligonucleotide aptamers suitable in application for both basic research and clinical purposes.

Several life-threatening cardiovascular syndromes, including myocardial infarction, stroke, and pulmonary embolism, are the clinical manifestation of thrombosis. Thrombosis is the formation of a blood clot inside a blood vessel, in which the blood clot is formed by accumulation of platelets and fibrin induced by the activation of coagulation factors. One of such coagulation factors is FXIII FXIII is a transglutaminase (TG) with tetrameric form (FXIII-$A_2B_2$) consisting of two A subunits (FXIII-A) and two B subunits (FXIII-B), in which FXIII-B serves as a carrier protein to stabilize FXIII-A. During later stage of thrombosis, FXIII is transformed into semi-activated FXIII (FXIII-$A_2'B_2$), and then the fully activated FXIII (FXIIIa; FXIII-$A_2'$) is produced by dissociation from FXIII-$B_2$, and catalyzed the cross-linking of fibrin by promoting the formation of a complex composed of proenzyme FXIII, prosubstrate fibrinogen, and activator thrombin, thus stabilizing the blood clot. According to the role of FXIII played in thrombosis, it is suitable to use FXIII as a target to develop an anti-thrombotic drug or thrombus imaging probe, so as to elaborate the fidelity of the anti-thrombotic drug targeting to thrombi. Alternatively, FXIII can be used to develop a detection system to trace the formation of thrombi in a subject.

In view of the foregoing, there exists in the related art a need for an aptamer capable of recognizing FXIII with desirable specificity and affinity.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to an aptamer specific to coagulation factor XIII (FXIII). The aptamer comprises a polynucleotide sequence of at least 90% identical to SEQ ID NO: 1. According to some embodiments of the present disclosure, the aptamer has the polynucleotide sequence of SEQ ID NO: 2, or SEQ ID NO: 3. According to one specific embodiment of the present disclosure, the aptamer has a polynucleotide sequence of SEQ ID NO: 4.

According to some embodiments of the present disclosure, the present aptamer may further be conjugated with a reporter, a contrast agent, a nanoparticle, or an anti-thrombotic agent.

In some embodiments, the reporter may be acridine orange, acridine yellow, alkaline phosphatase (AP), auramine, benzoxadiazole, bilirubin, biotin, blue fluorescent protein (BFP), 6'-carboxyfluorescein (FAM), cascade blue, cresyl violet, crystal violet, cyan fluorescent protein (CFP), cyanine, eosin, fluorescein, fluorescein isothiocyanate, glutathione-S-transferase (GST), green fluorescence protein (GFP), horseradish peroxidase (HRP), indocarbocyanine, malachite green, merocyanine, Nile blue, Nile red, nitrobenzoxadiazole, orotidine 5'-phosphate decarboxylase, oxacarbocyanine, peridinin chlorophyll, phycoerythrin, phthalocyanine, porphine, proflavine, pyridyloxazole, red fluorescent protein (RFP), rhodamine, thiacarbocyanine, thioredoxin (TRX), or yellow fluorescent protein (YFP).

In some embodiments, the contrast agent is a barium-sulfate, gadolinium-, or iodine-based contrast agent.

In some embodiments, the nanoparticle is aluminium oxide particle, boron particle, calcium particle, carbon nanotube, cerium oxide particle, clay particle, copper particle, diamond particle, gold particle, graphene particle, hydroxy acid particle, hydroxyapatite particle, iron particle, kojic acid particle, liposome, manganese particle, molybdenum particle, palladium particle, platinum particle, phosphorus particle, potassium particle, silicon dioxide particle, silver particle, sodium silicate particle, titanium dioxide particle, ytterbium trifluoride particle, zinc particle, zinc oxide particle, or zirconium dioxide particle.

In some embodiments, the anti-thrombotic agent is an anticoagulantor, an antiplatelet agent, or a thrombolytic agent.

Examples of the anticoagulantor include, but are not limited to, Acenocoumarol, Antithrombin III, Apixaban, Argatroban, Bemiparin, Betrixaban, Bivalirudin, Certoparin, Clorindione, Coumatetralyl, Dabigatran, Dalteparin, Danaparoid, Darexaban, Dermatan sulfate, Defibrotide, Desirudin, Dicoumarol, Diphenadione, Drotrecogin, Edoxaban, Efegatran, Enoxaparin, Ethyl biscoumacetate, Fondaparinux, Heparin, Heparinoid, Hirudin, Idraparinux, Inogatran, Lepirudin, Melagatran, Nadroparin, Otamixaban, Parnaparin, Phenindione, Phenprocoumon, Ramatroban, Reviparin, Rivaroxaban, Sulodexide, Tinzaparin, Tioclomarol, Warfarin, and Ximelagatran.

Further, exemplary antiplatelet agent is Abciximab, Acetylsalicylic acid, Aloxiprin, Aspirin, Beraprost, Cangrelor, Carbasalate calcium, Cilostazol, Clopidogrel, Cloricromen, Dipyridamole, Ditazole, Elinogrel, Eptifibatide, Iloprost, Indobufen, Orbofiban, Picotamide, Prasugrel, Prostacyclin, Roxifiban, Sibrafiban, Terbogrel, Terutroban, Thienopyridine, Ticagrelor, Ticlopidine, Tirofiban, Treprostinil, Triflusal, or Vorapaxar.

Moreover, the thrombolytic agent suitable for used in the present aptamer may be Alteplase, Ancrod, Anistreplase, Brinase, Desmoteplase, Fibrinolysin, Monteplase, Reteplase, Saruplase, Streptokinase, Tenecteplase, or Urokinase.

According to some embodiments of the present disclosure, the coagulation factor XIII (FXIII) may be derived from a variety of cells, such as chondrocyte, dendritic reticulum cell, dendrocyte, epithelioid cell, histiocyte, Hofbauer cell, intraglomerular mesangial cell, hepatocyte, Kupffer cell, LysoMac, macrophage, megakaryocyte, microglium, monocyte, osteoblast, osteoclast, osteocyte, plasma, or platelet.

Also encompassed in the present disclosure is a method for treating a disease associated with thrombosis in a subject using the aptamer described herein, in which the aptamer is conjugated with anti-thrombotic agent. The method at least comprises the step of administering to the subject an effective amount of the aforementioned aptamer.

In some embodiments, the anti-thrombotic agent conjugated with the present aptamer is an anticoagulantor, an antiplatelet agent, or a thrombolytic agent.

For example, the anticoagulantor is Acenocoumarol, Antithrombin III, Apixaban, Argatroban, Bemiparin, Betrixaban, Bivalirudin, Certoparin, Clorindione, Coumatetralyl, Dabigatran, Dalteparin, Danaparoid, Darexaban, Dermatan sulfate, Defibrotide, Desirudin, Dicoumarol, Diphenadione, Drotrecogin, Edoxaban, Efegatran, Enoxaparin, Ethyl biscoumacetate, Fondaparinux, Heparin, Heparinoid, Hirudin, Idraparinux, Inogatran, Lepirudin, Melagatran, Nadroparin, Otamixaban, Parnaparin, Phenindione, Phenprocoumon, Ramatroban, Reviparin, Rivaroxaban, Sulodexide, Tinzaparin, Tioclomarol, Warfarin, or Ximelagatran.

Also, the antiplatelet agent suitable for used in the present method may be Abciximab, Acetylsalicylic acid, Aloxiprin, Aspirin, Beraprost, Cangrelor, Carbasalate calcium, Cilostazol, Clopidogrel, Cloricromen, Dipyridamole, Ditazole, Elinogrel, Eptifibatide, Iloprost, Indobufen, Orbofiban, Picotamide, Prasugrel, Prostacyclin, Roxifiban, Sibrafiban, Terbogrel, Terutroban, Thienopyridine, Ticagrelor, Ticlopidine, Tirofiban, Treprostinil, Triflusal, or Vorapaxar.

In addition, examples of the thrombolytic agent are Alteplase, Ancrod, Anistreplase, Brinase, Desmoteplase, Fibrinolysin, Monteplase, Reteplase, Saruplase, Streptokinase, Tenecteplase, or Urokinase.

According to some preferred embodiments of the present disclosure, the subject in need thereof is a human.

According to some embodiments of the present disclosure, the disease associated with thrombosis is venous thrombosis or arterial thrombosis.

Exemplary venous thrombosis includes, but is not limited to, branch retinal vein occlusion, Budd-Chiari syndrome, cavernous sinus thrombosis, central retinal vein occlusion, cerebral venous sinus thrombosis, deep vein thrombosis, jugular vein thrombosis, mesenteric vein thrombosis, Paget-Schroetter disease, parodoxical embolism, portal vein thrombosis, pulmonary embolism, renal vein thrombosis, and splenic vein thrombosis.

Also, examples of the arterial thrombosis include, but are not limited to, hepatic artery thrombosis, limb ischemia, myocardial infarction, or stroke.

According to some embodiments of the present disclosure, the pharmaceutical composition may be administered to the subject via any suitable routes such as oral, intracranial, intraspinal, intrathecal, intramedullar, intracerebral, intracerebroventricular, intravenous, intraarterial, intracardial, intracutaneous, subcutaneous, transdermal, intraperitoneal, or intramuscular routes.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects and advantages of the present invention will become better understood with reference to the following description, appended claims and the accompanying drawings, where:

DESCRIPTION

Figure 1:
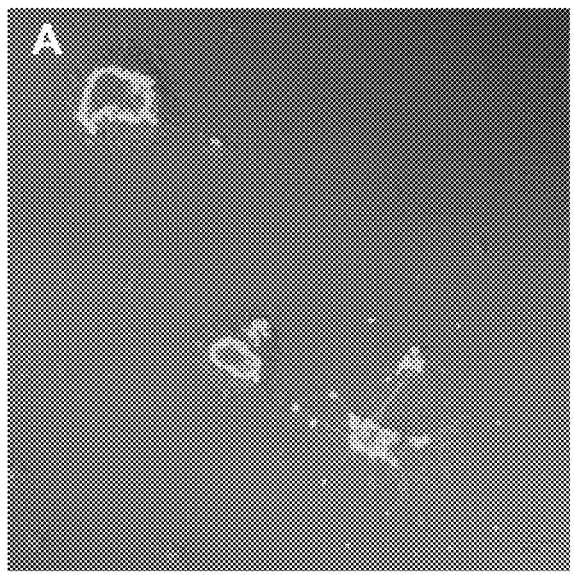
FIG. 1 is confocal laser scanning microscopy images in accordance with one embodiment of the present disclosure. Panel (A): targeting of the 6'-carboxyfluorescein (FAM)-conjugated FAT2 toward the fibrin and activated platelets. Panel (B): targeting of FAM-conjugated N-DNA, a random aptamer as a negative control, toward the fibrin and activated platelets. All the photographs are merged images of FAM (green, Ex. 495 nm, Em. 517 nm) and visible light (showing the presence of the fibrin and activated platelets).
Figure 1:
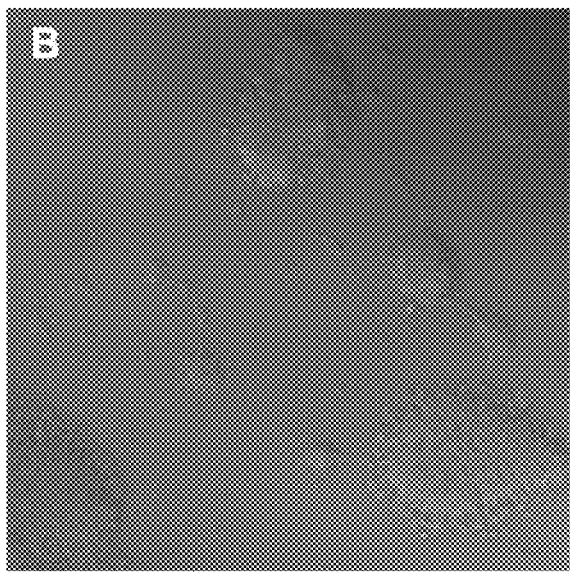

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a," "an," and "the" include the plural reference unless the context clearly dictates otherwise. Also, as used herein and in the claims, the terms "at least one" and "one or more" have the same meaning and include one, two, three, or more. The practice of the present invention will employ, unless otherwise indicated, conventional techniques of molecular biology, microbiology, recombinant DNA, and immunology, which are within the skill of the art. Such techniques are explained fully in the literature.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "aptamer" as used herein refers to a single- or double-stranded nucleic acid that is able to strongly and specifically bind to coagulation factor XIII (FXIII). The aptamer of the present disclosure may be constituted by DNAs alone, RNAs alone, or DNAs and RNAs in combination. Optionally, the aptamer of the present disclosure may further comprise non-natural nucleotide(s). The "non-natural nucleotide" refers to an artificially constructed or artificially chemically modified nucleotide that is similar in property and/or structure to the natural nucleotide. Examples of the non-natural nucleotide include abasic nucleoside, arabinonucleoside, 2'-deoxyuridine, α-deoxyribonucleoside, β-L-deoxyribonucleoside, and other glycosylated nucleosides. The glycosylated nucleosides include glycosylated nucleosides having substituted pentose (2'-O-methylribose, 2'-deoxy-2'-fluororibose, 3'-O-methylribose, or 1',2'-deoxyribose), arabinose, substituted arabinose sugar, substituted hexose, or alpha anomer. The non-natural nucleoside of the present disclosure may be an artificially constructed base analog or an artificially chemically modified base. Examples of the "base analog" include a 2-oxo(1H)-pyridin-3-yl group, a 5-substituted 2-oxo(1H)-pyridin-3-yl group, a 2-amino-6-(2-thiazolyl)purin-9-yl group, and a 2-amino-6-(2-oxazolyl)purin-9-yl group. Examples of the "modified base" include modified pyrimidine (e.g., 5-hydroxycytosine, 5-fluorouracil and 4-thiouracil), modified purine (e.g., 6-methyladenine and 6-thioguanosine), and other heterocyclic bases.

As used herein, the term "sequence identity" means the degree of identity between any given query sequence and a subject sequence. The percentage of "sequence identity" in the comparison window by comparing two optimally aligned sequences over a determined, wherein a fragment of the nucleotide sequence in the comparison window may be compared to the reference sequence (which does not comprise additions or deletions) may be they comprise additions or deletions (e.g., gaps or protrusions) for optimal alignment of two sequences pair. The percentages are performed by: determining the number of positions identical nucleic acid base occurs in both sequences to yield the number of matched positions, the total number of positions in the comparison window by dividing the number of matched positions, and multiplying the result by 100 to obtain the sequence the percent identity. The output is relative to the query sequence percent identity of the subject sequence. Two for determining percent sequence identity between the various methods specific polynucleotide sequences are known to those skilled in the art. For example, one method is to use the Basic Local Alignment Search Tool (BLAST) tool, the tool finds regions of local similarity (www.ncbi.nlm.nih.gov/BLAST/) between sequences.

The terms "conjugated" or "conjugate" are used herein to refer to two or more entities that are linked by direct or indirect covalent or non-covalent interaction. In some embodiments, the present aptamer is conjugated with a reporter molecule (e.g., a fluorescent molecule). In other embodiments, the present aptamer is conjugated with a contrast agent (e.g., a barium-sulfate-based contrast agent). In still other embodiments, the present aptamer is conjugated with a nanoparticle (e.g., a gold particle, or a liposome). In yet other embodiments, the present aptamer is conjugated with an anti-thrombotic agent (e.g., an anticoagulator, an antiplatelet drug, or a thrombolytic agent).

The terms "treatment" and "treating" as used herein may refer to a curative or palliative measure. In particular, the term "treating" as used herein refers to the application or administration of the present aptamer, which is conjugated with an anti-thrombotic agent to a subject, who suffers from a disease associated with thrombosis, a symptom associated with thrombosis, a disease or disorder secondary to thrombosis, with the purpose to partially or completely alleviate, ameliorate, relieve, delay onset of, inhibit progression of, reduce severity of, and/or reduce incidence of one or more symptoms or features of thrombosis.

The term "subject" or "patient" refers to an animal including the human species that is treatable with the compositions and/or methods of the present disclosure. The term "subject" or "patient" intended to refer to both the male and female gender unless one gender is specifically indicated. Accordingly, the term "subject" or "patient" comprises any mammal which may benefit from treatment of thrombosis. Examples of a "subject" or "patient" treatable with the present compositions and/or methods include, but are not limited to, a human, rat, mouse, guinea pig, monkey, pig, goat, cow, horse, dog, cat, bird and fowl. In an exemplary embodiment, the patient is a human.

The term "administered," "administering" or "administration" are used interchangeably herein to refer to directly give a pharmaceutical composition of the present disclosure to a subject.

The term "an effective amount" as used herein refers to an amount effective, at dosages, and for periods of time necessary, to achieve the desired result with respect to the present aptamer targeting FXIII and/or the treatment of thrombosis.

II. Description of the Invention

The practices of the present disclosure are described hereinafter in detail with respect to an aptamer against FXIII, and its uses in targeting FXIII and/or treating thrombosis in a subject by delivering an anti-thrombotic agent to a thrombotic area with the aid of the present aptamer.

1. The Aptamer of the Present Disclosure

The aptamer of the present disclosure corresponds to, as described above in the "I. Definition" section, a natural nucleic acid such as DNA, RNA or a combination thereof. Also, the nucleic acid may partially or wholly comprise non-natural nucleotide. Preferably, the aptamer of the present disclosure is a single-stranded DNA aptamer.

According to embodiments of the present disclosure, the present aptamer is about 5 to 80 nucleotides (nt) in length; preferably, 35 to 50 nt in length; such as 35, 36, 37, 38, 39, 40, 41, 42, 43, 44, 45, 46, 47, 48, 49 or 50 nt in length. Nevertheless, the region of the aptamer that plays the role of target contacting is usually 10 to 20 nt. In some embodiments, the present aptamer may intramolecularly comprise one or more double-stranded regions. The "double-stranded region" refers to a region formed by consecutive base pairs between the nucleotide strands constituting the nucleic acid molecular. The length of the consecutive base pairs may be 2 to 10 bp, such as 2 to 5 bp, 2 to 6 bp, 2 to 7 bp, 2 to 8 bp, 2 to 9 bp or 2 to 10 bp. The aptamer may comprise two or more double-stranded regions. In such case, each doubled stranded region is constituted by base pairs that are the same or different between the double-stranded regions. Each double-stranded region may be interrupted by a region (such as mismatch sites, gaps, and internal loop structures) that is not base-paired between the strands. Alternatively, each double stranded region may be continuous.

In specific embodiments of the present aptamer comprises a polynucleotide sequence at least 90% (e.g., 90%, 91%, 92%, 93%, 94%, 95%, 96%, 97%, 98%, 99%, or 100%) identical to SEQ ID NO: 1. In some embodiments of the present aptamer comprises a polynucleotide sequence at least 94% (e.g., 94%, 95%, 96%, 97%, 98%, 99%, or 100%) identical to SEQ ID NO: 1. In more specific embodiments, the present aptamer has the polynucleotide sequence of SEQ ID NO: 2, or SEQ ID NO: 3. Alternatively, the present aptamer has the polynucleotide sequence of SEQ ID NO: 4. According to embodiments of the present disclosure, the present aptamer bind to FXIII with $K_d$ value in the nanomolar range.

According to some embodiments of the present disclosure, the present aptamer may be conjugated with a reporter, a contrast agent, a nanoparticle, or an anti-thrombotic agent. In some embodiments, the present aptamer is conjugated with a reporter. According to one embodiment, said reporter is a fluorescent dye. In another embodiment, said reporter is a ligand. The conjugation can be achieved by methods familiar to a skilled artisan. For example, the 3' or 5' primary amines can be coupled to various molecules during chemical synthesis of nucleic acid; or the conjugation can be achieved via classic carbodiimide, aldehyde, diazonium, or other approaches that take advantage of the much greater chemical reactivity of primary alkyl amine tags versus aryl amines on the nucleotides themselves.

Exemplary reporters include, but are not limited to, acridine orange, acridine yellow, alkaline phosphatase (AP), auramine, benzoxadiazole, bilirubin, biotin, blue fluorescent protein (BFP), 6'-carboxyfluorescein (FAM), cascade blue, cresyl violet, crystal violet, cyan fluorescent protein (CFP), cyanine, eosin, fluorescein, fluorescein isothiocyanate, glutathione-S-transferase (GST), green fluorescence protein (GFP), horseradish peroxidase (HRP), indocarbocyanine, malachite green, merocyanine, Nile blue, Nile red, nitrobenzoxadiazole, orotidine 5'-phosphate decarboxylase, oxacarbocyanine, peridinin chlorophyll, phycoerythrin, phthalocyanine, porphine, proflavine, pyridyloxazole, red fluorescent protein (RFP), rhodamine, thiacarbocyanine, thioredoxin (TRX), and yellow fluorescent protein (YFP). In one preferred embodiment, the reporter is FAM. In another preferred embodiment, the reporter is biotin. In still another preferred embodiment, the reporter is cyanine.

Alternatively, the present aptamer may be conjugated with a contrast agent; such contrast agent is a barium-sulfate-based contrast agent, a gadolinium-based contrast agent, or an iodine-based contrast agent.

In other embodiments, the present aptamer may be conjugated with a nanoparticle. Said nanoparticle includes, but is not limited to, aluminium oxide particle, boron particle, calcium particle, carbon nanotube, cerium oxide particle, clay particle, copper particle, diamond particle, gold particle, graphene particle, hydroxy acid particle, hydroxyapatite particle, iron particle, kojic acid particle, liposome, manganese particle, molybdenum particle, palladium particle, platinum particle, phosphorus particle, potassium particle, silicon dioxide particle, silver particle, sodium silicate particle, titanium dioxide particle, ytterbium trifluoride particle, zinc particle, zinc oxide particle, and zirconium dioxide particle.

In still other embodiments, the present aptamer may be conjugated with an anti-thrombotic agent. Three classes of anti-thrombotic agent are available, one is anticoagulantor, and one is antiplatelet agent, and the other is thrombolytic agent.

In terms of the anticoagulantor, examples include, but are not limited to, Acenocoumarol, Antithrombin III, Apixaban, Argatroban, Bemiparin, Betrixaban, Bivalirudin, Certoparin, Clorindione, Coumatetralyl, Dabigatran, Dalteparin, Danaparoid, Darexaban, Dermatan sulfate, Defibrotide, Desirudin, Dicoumarol, Diphenadione, Drotrecogin, Edoxaban, Efegatran, Enoxaparin, Ethyl biscoumacetate, Fondaparinux, Heparin, Heparinoid, Hirudin, Idraparinux, Inogatran, Lepirudin, Melagatran, Nadroparin, Otamixaban, Parnaparin, Phenindione, Phenprocoumon, Ramatroban, Reviparin, Rivaroxaban, Sulodexide, Tinzaparin, Tioclomarol, Warfarin, and Ximelagatran.

Exemplary antiplatelet agent is Abciximab, Acetylsalicylic acid, Aloxiprin, Aspirin, Beraprost, Cangrelor, Carbasalate calcium, Cilostazol, Clopidogrel, Cloricromen, Dipyridamole, Ditazole, Elinogrel, Eptifibatide, Iloprost, Indobufen, Orbofiban, Picotamide, Prasugrel, Prostacyclin, Roxifiban, Sibrafiban, Terbogrel, Terutroban, Thienopyridine, Ticagrelor, Ticlopidine, Tirofiban, Treprostinil, Triflusal, or Vorapaxar.

The thrombolytic agent that may be used in the present disclosure is Alteplase, Ancrod, Anistreplase, Brinase, Desmoteplase, Fibrinolysin, Monteplase, Reteplase, Saruplase, Streptokinase, Tenecteplase, or Urokinase.

According to some embodiments of the present disclosure, the coagulation factor XIII (FXIII) may be derived from chondrocyte, dendritic reticulum cell, dendrocyte, epithelioid cell, histiocyte, Hofbauer cell, intraglomerular mesangial cell, hepatocyte, Kupffer cell, LysoMac, macrophage, megakaryocyte, microglium, monocyte, osteoblast, osteoclast, osteocyte, plasma, or platelet.

2. Methods for Treating Thrombosis

In another aspect, the present disclosure is related to the uses of the present aptamer in methods for treating a disease associated with thrombosis in a subject, especially for the subject that has the FXIII-presenting thrombi. The method comprises administering to the subject an effective amount of the present aptamer, in which the aptamer is conjugated with a therapeutic agent, preferably an anti-thrombotic agent.

Preferably, the subject treatable by the present method is a mammal. In one example, the subject is a mouse. In another example, the subject is a human.

Also, the disease associated with thrombosis treatable by the present method may be venous thrombosis or arterial thrombosis.

Examples of the venous thrombosis include, but are not limited to, branch retinal vein occlusion, Budd-Chiari syndrome, cavernous sinus thrombosis, central retinal vein occlusion, cerebral venous sinus thrombosis, deep vein thrombosis, jugular vein thrombosis, mesenteric vein thrombosis, Paget-Schroetter disease, parodoxical embolism, portal vein thrombosis, pulmonary embolism, renal vein thrombosis, and splenic vein thrombosis. Examples of arterial thrombosis include, but are not limited to, hepatic artery thrombosis, limb ischemia, myocardial infarction, stroke, and the like.

In the present method, the present aptamer can be formulated into suitable formulations for administering by a suitable route known to those skilled in the art, including oral, intracranial, intraspinal, intrathecal, intramedullar, intracerebral, intracerebroventricular, intravenous, intraarterial, intracardial, intracutaneous, subcutaneous, transdermal, intraperitoneal, or intramuscular administration. Generally, the most appropriate route of administration will depend upon a variety of factors including the nature of the agent (e.g., its stability in circulation), and/or the condition of the subject (e.g., whether the subject is able to tolerate intraperitoneal administration or intravenous administration).

The anti-thrombotic agent conjugated with the present aptamer may be an anticoagulator, an antiplatelet agent, or a thrombolytic agent.

The anticoagulator includes, but is not limited to, Acenocoumarol, Antithrombin III, Apixaban, Argatroban, Bemiparin, Betrixaban, Bivalirudin, Certoparin, Clorindione, Coumatetralyl, Dabigatran, Dalteparin, Danaparoid, Darexaban, Dermatan sulfate, Defibrotide, Desirudin, Dicoumarol, Diphenadione, Drotrecogin, Edoxaban, Efegatran, Enoxaparin, Ethyl biscoumacetate, Fondaparinux, Heparin, Heparinoid, Hirudin, Idraparinux, Inogatran, Lepirudin, Melagatran, Nadroparin, Otamixaban, Parnaparin, Phenindione, Phenprocoumon, Ramatroban, Reviparin, Rivaroxaban, Sulodexide, Tinzaparin, Tioclomarol, Warfarin, or Ximelagatran.

Examples of the antiplatelet agent is Abciximab, Acetylsalicylic acid, Aloxiprin, Aspirin, Beraprost, Cangrelor, Carbasalate calcium, Cilostazol, Clopidogrel, Cloricromen, Dipyridamole, Ditazole, Elinogrel, Eptifibatide, Iloprost, Indobufen, Orbofiban, Picotamide, Prasugrel, Prostacyclin, Roxifiban, Sibrafiban, Terbogrel, Terutroban, Thienopyridine, Ticagrelor, Ticlopidine, Tirofiban, Treprostinil, Triflusal, or Vorapaxar.

The thrombolytic agent is, for example, Alteplase, Ancrod, Anistreplase, Brinase, Desmoteplase, Fibrinolysin, Monteplase, Reteplase, Saruplase, Streptokinase, Tenecteplase, or Urokinase.

3. Methods for Tracing Thrombosis

In yet another aspect of the present disclosure, a method of tracing the thrombosis of a subject in vitro or in vivo using the present aptamer as a thrombus imaging probe is provided. The method for in vitro tracing includes the step of:
 (a) providing an isolated biological sample from the subject;
 (b) incubating a sufficient amount of the present aptamer with the isolated biological sample; and
 (c) detecting the presence of the present aptamer within the isolated biological sample;
wherein, the present aptamer is conjugated with a reporter, a contrast agent, or a nanoparticle.

In the step (a), the isolated biological sample may be a mucus sample, a plasma sample, a saliva sample, a serum sample, a sputum sample, a tissue sample, a urine sample, or a whole blood sample. In one specific embodiment, the isolated biological sample is a plasma sample. The isolated biological sample may be further processed, such as by treating with calcium chloride, and/or coated onto a slide glass, before proceeding to the step (b).

In the step (b), the condition for the incubation (such as the amount of the present aptamer to be added, and/or time, temperature, pH, buffer system required for achieving the purpose of binding the present aptamer with the biological sample) is known to a skilled artisan.

In some preferred embodiments, the present aptamer is conjugated with a reporter, such as FAM or biotin.

The amount of the present aptamer sufficient to bind to the FXIII-containing thormbi in the biological sample will vary with the type of reporter conjugated with the aptamer, and the method for detecting the reporter. In general, about 100-1000 nM is required for in vitro incubation; such as 100, 150, 200, 250, 300, 350, 400, 450, 500, 550, 600, 650, 700, 750, 800, 850, 900, 950, or 1,000 nM. In some in vitro embodiments, about 300-500 nM of the present aptamer is required in the step (b).

In the step (c), the present aptamer having bound to the FXIII-presenting cell in the biological sample can be detected by various methods, which depend on the type of the reporter conjugated with the aptamer. For example, in the case when a fluorescent dye (e.g., FAM) is conjugated to the present aptamer, the aptamer-FXIII complex can be detected by fluorescent microscopy or flow cytometry assay. Alternatively, in the case when a ligand (e.g., biotin) is conjugated to the aptamer, then the aptamer-FXIII complex can be detected by incubating with HRP-conjugated streptavidin and with substrates for HRP colorization.

As to the method for in vivo tracing, the method includes the step of:
 (a) administering a sufficient amount of the present aptamer to the subject; and
 (b) detecting the presence of the present aptamer within the subject;
wherein, the present aptamer is conjugated with a reporter, a contrast agent, or a nanoparticle.

In the step (a), the amount of the present aptamer sufficient to bind to thormbi that contains FXIII in vivo is about 0.1-10 mg/kg, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, or 10.0 mg/kg. Preferably, the amount is about 0.5-2.0 mg/kg. In one specific example, the amount of the present aptamer administered to the subject to detect the FXIII-containing thormbi is about 1.2 mg/kg.

As to the detection (or the step (b)), suitable method is chosen in accordance with the type of the reporter molecules conjugated therewith the present aptamer. For example, in the case when a fluorescent dye (e.g., Cy5.5) is conjugated with the aptamer, then the FXIII-aptamer complex can be detected by in vivo fluorescent imaging technique.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

1. Blood Samples

Human whole blood was collected from healthy donor (20 to 35 years old) via venipuncture and anticoagulated with 3.2% sodium citrate in a ratio of 1 part anticoagulant to 9 parts blood.

2. Confocal Microscopy

Cell images were acquired by confocal fluorescence microscopy. Briefly, the plasma was mixed with calcium chloride, added onto a slide glass coated with fibrin, and incubated for 5 mins. After incubation, the slide glass was washed using phosphate-buffered saline (PBS), and FAM-conjugated aptamers were added onto the slide glass and incubated for 30 mins. The slide glass was washed and mounted, and the fluorescence images of the slide glass were obtained under a confocal fluorescence microscope.

3. Flow Cytometry

The whole blood was centrifuged for several times to isolate the un-activated platelets, which were then activated by addition of PBS and thrombin receptor activating peptide (TRAP). The FAM-conjugated aptamers were added into the activated platelets, and incubated for 30 mins. The fluorescence intensity was determined using a flow cytometer by counting 10,000 events.

4. Dot Blot Analysis

Purified FXIII was blotted on a nitrocellulose (NC) membrane, and air-dried for 1 hr. Then a mixture of BSA, PBS, and Polyoxyethylene(20)sorbitan monolaurate (TWEEN™ 20) was added to the NC membrane and incubated for 1 hr, and following biotin-conjugated aptamers were added to the NC membrane and incubated for another 1 hr. The NC membrane was washed thrice using a washing buffer of PBS and Tween 20, and horseradish peroxidase (HRP)-conjugated streptavidin was added to the NC membrane and incubated for 1 hr. For coloration, a substrate of HRP was added to the NC membrane after washing, and the images of the NC membrane were acquired by a X-ray film processor.

5. Animal Model

Male Sprague Dawley rats were used in the present study. All animals were maintained in the animal facility with controlled temperature (21-24° C.), humidity (45-70%) and a 12 h/12 h light/dark cycle with food and water provided ad libitum. For the microcirculation embolism model, the rats (330±7 g, n=26) were anesthetized using Inactin® (100 mg/kg; ip.). The testes were removed, and urinary bladder was cannulated. There is a T-shape vessel formed by the intersection of the pudic epigastric artery, the femoral artery, the iliac artery in the abdomen, and the vessel branches that do not reach the cremaster vasculature were cut. The femoral artery was cannulated, and an infusion was given through the cannulation. The cremaster muscle was then placed in situ, and rose bengal dye (50 mg/kg; iv.) was applied. Then, laser of 540 nm (3 mW) was given for 10-15 min to induce endothelium damage and thrombus formation. The in vivo fluorescent imaging system (VIEWORKS In Vivo Elite) was used to detect the perfusion, the retention of the aptamer, and the blood flow within the tissue. During the experiments, Cy5.5-labeled control aptamer, Cy5.5-labeled FXIII-binding aptamer, and Cy5.5 labeled thrombin-binding aptamers TBA15/29 and NU172 (1.2 mg/kg) were given in order to evaluate the targeting ability of the aptamers toward the thrombi in the rats.

6. Statistics Analysis

Descriptive statistics (mean, standard deviation [SD], standard error of the mean [SEM]) were used to assess normality. The binding of FXIII-binding aptamers to platelets by flow cytometry was compared using two-way ANOVA with Duncan post-hoc testing by Statistica software (StatSoft, Tulsa, Okla., USA). $P<0.05$ was considered statistically significant.

Example 1 Characterization of the Present Aptamers

Figure 2:
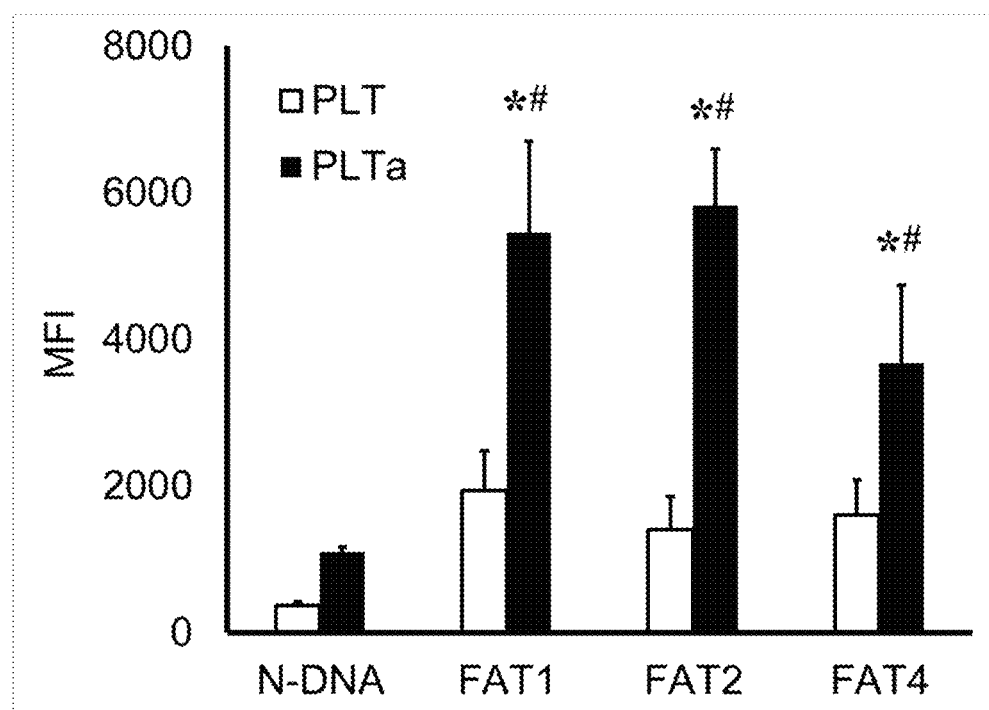
FIG. 2 is the bar graph of flow cytometry results in accordance with one embodiment of the present disclosure, delineating targeting of the indicated FAM-conjugated aptamers toward un-activated platelets (designated as PLT), and activated platelets (designated as PLTa). MFI: mean fluorescence intensity; *: $P<0.05$ vs. PLT, #: $P<0.05$ vs. N-DNA.
Figure 3:
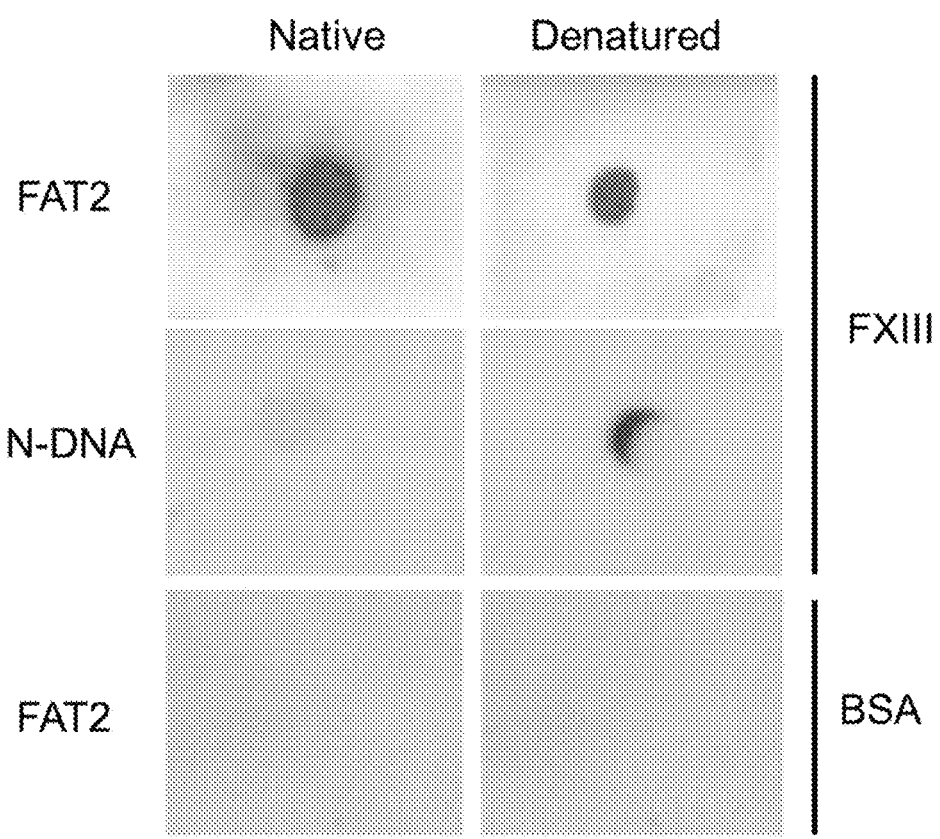
FIG. 3 are the results of dot blot in accordance with one embodiment of the present disclosure, which depicts the binding ability of the indicated biotin-conjugated aptamers toward FXIII or bovine serum albumin (BSA) under native (left) or denatured (right) condition.

The present aptamers were synthesized and respectively termed FAT1 (SEQ ID NO: 2), FAT2 (SEQ ID NO: 3), and FAT4 (SEQ ID NO: 4); relevant description of the aptamers as summarized in Table 1. In the present Example, the specificity of each aptamer was evaluated, and results are illustrated in FIGS. 1 to 3.

TABLE 1

Aptamers in the present disclosure

| Name | SEQ ID NO | Sequence (5'-3') |
|---|---|---|
| FAT 1 | 2 | CAGCACGACGGGATTCGGGTCGGCAAGGGGTGTGCGGGGGCGTGCTG |
| FAT2 | 3 | CGCAGCATCATTCGGGTCGGGAAGGGGTGTACGGGGCTGCG |
| FAT4 | 4 | CAGCAGGGAGTCCAGTAGGGTCGGTGTGGGTCGTAAGTTGGGTGCTG |
| FAT2-19 | 1 | TCGGGTCGGGAAGGGGTGT |

As illustrated in FIG. 1, panel (A), FAT2 exhibited good affinity and specificity to fibrin, as well as the activated platelets, where FXIII was expressed thereon. By contrast, the signal of the random aptamer N-DNA was not detected on the same sample (FIG. 1, panel (B)). These results evidence that FXIII specific aptamers FATX alone can specifically bind to the target FXIII.

The specificity of the present aptamers to FXIII was further evaluated by flow cytometry. The data was presented in bar graphs to illustrate the binding activity of each indicated aptamer to either the un-activated platelets (designated as PLT) or the activated platelets (designated as PLTa). As depicted in FIG. 2, none of the aptamers (i.e., N-DNA (a negative control aptamer), FAT1, FAT2, and FAT4) exhibited significant binding activity to the un-activated platelets. By contrast, all aptamers, including FAT1, FAT2, and FAT4, exhibited evident binding activity to the activated platelets as compared to the control (i.e., N-DNA). Taken together, the data in this example confirmed that the present aptamers specifically bond to the activated platelets rather than the un-activated platelets.

To further characterize binding condition of the present aptamers to FXIII, a dot blot assay was performed.

Reference is made to FIG. 3, the binding under native condition is provided in the left panel, while that under denatured condition is illustrated in the right panel. In the left panel of FIG. 3, only FAT2 exhibited the binding activity to FXIII rather than BSA, while N-DNA did not bind to FXIII, suggesting that FAT2 may specifically target FXIII without cross reacting with the off-target BSA under native condition. Moreover, in the right panel of FIG. 3, FAT2 still exhibited a strong binding to FXIII, as compared to N-DNA which only showed a slightly binding activity, and FAT2 remained not bound to BSA, suggesting FAT2 may still specifically target FXIII without cross reacting with BSA under denatured condition. Taken together, the results confirmed that FAT2 may target FXIII at both native and denatured conditions.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An aptamer specific to coagulation factor XIII (FXIII) comprising a polynucleotide sequence at least 90% identical to SEQ ID NO: 1, wherein the aptamer has the polynucleotide sequence of SEQ ID NO: 2, or SEQ ID NO: 3, or SEQ ID NO: 4.

2. The aptamer of claim 1, wherein the aptamer further comprising a reporter, a contrast agent, a nanoparticle, or an anti-thrombotic agent conjugated thereto.

3. The aptamer of claim 2, wherein the reporter is acridine orange, acridine yellow, alkaline phosphatase (AP), auramine, benzoxadiazole, bilirubin, biotin, blue fluorescent protein (BFP), 6'-carboxyfluorescein (FAM), cascade blue, cresyl violet, crystal violet, cyan fluorescent protein (CFP), cyanine, eosin, fluorescein, fluorescein isothiocyanate, glutathione-S-transferase (GST), green fluorescence protein (GFP), horseradish peroxidase (HRP), indocarbocyanine, malachite green, merocyanine, Nile blue, Nile red, nitrobenzoxadiazole, orotidine 5'-phosphate decarboxylase, oxacarbocyanine, peridinin chlorophyll, phycoerythrin, phthalocyanine, porphine, proflavine, pyridyloxazole, red

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
tcgggtcggg aagggtgt                                                19

<210> SEQ ID NO 2
<211> LENGTH: 47
<212> TYPE: DNA
<213> ORGANISM: Artificial Sequence
<220> FEATURE:
<223> OTHER INFORMATION: Synthetic

<400> SEQUENCE: 2
cagcacgacg ggattcgggt cggcaagggg tgtgcgggggg cgtgctg                47

<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3
cgcagcatca ttcgggtcgg aagggtgt acggggctgc g                        41

<210> SEQ ID NO 4
<211> LENGTH: 47
<212> TYPE: DNA
<213> ORGANISM: Artificial Sequence
<220> FEATURE:
<223> OTHER INFORMATION: Synthetic

<400> SEQUENCE: 4
cagcagggag tccagtaggg tcggtgtggg tcgtaagttg ggtgctg                 47 fluorescent protein (RFP), rhodamine, thiacarbocyanine, thioredoxin (TRX), or yellow fluorescent protein (YFP).

4. The aptamer of claim 2, wherein the contrast agent is a barium-sulfate-, gadolinium-, or iodine-based contrast agent.

5. The aptamer of claim 2, wherein the nanoparticle is aluminium oxide particle, boron particle, calcium particle, carbon nanotube, cerium oxide particle, clay particle, copper particle, diamond particle, gold particle, graphene particle, hydroxy acid particle, hydroxyapatite particle, iron particle, kojic acid particle, liposome, manganese particle, molybdenum particle, palladium particle, platinum particle, phosphorus particle, potassium particle, silicon dioxide particle, silver particle, sodium silicate particle, titanium dioxide particle, ytterbium tri fluori de particle, zinc particle, zinc oxide particle, or zirconium dioxide particle.

6. The aptamer of claim 2, wherein the anti-thrombotic agent is an anticoagulantor, an antiplatelet agent, or a thrombolytic agent.

7. The aptamer of claim 6, wherein the anticoagulantor is selected from the group consisting of, Acenocoumarol, Antithrombin III, Apixaban, Argatroban, Bemiparin, Betrixaban, Bivalirudin, Certoparin, Clorindione, Coumatetralyl, Dabigatran, Dalteparin, Danaparoid, Darexaban, Dermatan sulfate, Defibrotide, Desirudin, Dicoumarol, Diphenadione, Drotrecogin, Edoxaban, Efegatran, Enoxaparin, Ethyl biscoumacetate, Fondaparinux, Heparin, Heparinoid, Hirudin, Idraparinux, Inogatran, Lepirudin, Melagatran, Nadroparin, Otamixaban, Parnaparin, Phenindione, Phenprocoumon, Ramatroban, Reviparin, Rivaroxaban, Sulodexide, Tinzaparin, Tioclomarol, Warfarin, and Ximelagatran.

8. The aptamer of claim 6, wherein the antiplatelet agent is selected from the group consisting of, Abciximab, Acetylsalicylic acid, Aloxiprin, Aspirin, Beraprost, Cangrelor, Carbasalate calcium, Cilostazol, Clopidogrel, Cloricromen, Dipyridamole, Ditazole, Elinogrel, Eptifibatide, Iloprost, Indobufen, Orbofiban, Picotamide, Prasugrel, Prostacyclin, Roxifiban, Sibrafiban, Terbogrel, Terutroban, Thienopyridine, Ticagrelor, Ticlopidine, Tirofiban, Treprostinil, Triflusal, and Vorapaxar.

9. The aptamer of claim 6, wherein the thrombolytic agent is selected from the group consisting of, Alteplase, Ancrod, Anistreplase, Brinase, Desmoteplase, Fibrinolysin, Monteplase, Reteplase, Saruplase, Streptokinase, Tenecteplase, and Urokinase.

10. A method for treating a disease associated with thrombosis in a subject, comprising administering to the subject an effective amount of the aptamer of claim 6.

11. The method of claim 10, wherein the anticoagulantor is selected from the group consisting of, Acenocoumarol, Antithrombin III, Apixaban, Argatroban, Bemiparin, Betrixaban, Bivalirudin, Certoparin, Clorindione, Coumatetralyl, Dabigatran, Dalteparin, Danaparoid, Darexaban, Dermatan sulfate, Defibrotide, Desirudin, Dicoumarol, Diphenadione, Drotrecogin, Edoxaban, Efegatran, Enoxaparin, Ethyl biscoumacetate, Fondaparinux, Heparin, Heparinoid, Hirudin, Idraparinux, Inogatran, Lepirudin, Melagatran, Nadroparin, Otamixaban, Parnaparin, Phenindione, Phenprocoumon, Ramatroban, Reviparin, Rivaroxaban, Sulodexide, Tinzaparin, Tioclomarol, Warfarin, and Ximelagatran.

12. The method of claim 10, wherein the antiplatelet agent is selected from the group consisting of, Abciximab, Acetylsalicylic acid, Aloxiprin, Aspirin, Beraprost, Cangrelor, Carbasalate calcium, Cilostazol, Clopidogrel, Cloricromen, Dipyridamole, Ditazole, Elinogrel, Eptifibatide, Iloprost, Indobufen, Orbofiban, Picotamide, Prasugrel, Prostacyclin, Roxifiban, Sibrafiban, Terbogrel, Terutroban, Thienopyridine, Ticagrelor, Ticlopidine, Tirofiban, Treprostinil, Triflusal, and Vorapaxar.

13. The method of claim 10, wherein the thrombolytic agent is selected from the group consisting of, Alteplase, Ancrod, Anistreplase, Brinase, Desmoteplase, Fibrinolysin, Monteplase, Reteplase, Saruplase, Streptokinase, Tenecteplase, and Urokinase.

14. The method of claim 10, wherein the subject is a human.

15. The method of claim 10, wherein the disease associated with thrombosis is venous thrombosis or arterial thrombosis.

16. The method of claim 15, wherein the venous thrombosis is branch retinal vein occlusion, BuddChiari syndrome, cavernous sinus thrombosis, central retinal vein occlusion, cerebral venous sinus thrombosis, deep vein thrombosis, jugular vein thrombosis, mesenteric vein thrombosis, PagetSchroetter disease, parodoxical embolism, portal vein thrombosis, pulmonary embolism, renal vein thrombosis, or splenic vein thrombosis.

17. The method of claim 15, wherein the arterial thrombosis is hepatic artery thrombosis, limb ischemia, myocardial infarction, or stroke.

\* \* \* \* \*